: US011648352B2

(12) United States Patent
Nakano et al.

(10) Patent No.: US 11,648,352 B2
(45) Date of Patent: May 16, 2023

(54) MEDICAL SYRINGE, GASKET TO BE USED FOR SYRINGE, AND GASKET PRODUCTION METHOD

(71) Applicant: SUMITOMO RUBBER INDUSTRIES, LTD., Kobe (JP)

(72) Inventors: Hiroaki Nakano, Kobe (JP); Yuki Sakashita, Kobe (JP); Yoshikazu Masuyama, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 1296 days.

(21) Appl. No.: 16/116,093

(22) Filed: Aug. 29, 2018

(65) Prior Publication Data

US 2018/0369489 A1 Dec. 27, 2018

Related U.S. Application Data

(62) Division of application No. 15/640,816, filed on Jul. 3, 2017, now Pat. No. 10,363,371.

(30) Foreign Application Priority Data

Aug. 3, 2016 (JP) ................................ 2016-153119

(51) Int. Cl.
*B29C 35/02* (2006.01)
*A61M 5/315* (2006.01)
(Continued)

(52) U.S. Cl.
CPC ...... *A61M 5/31513* (2013.01); *A61M 5/3129* (2013.01); *B29C 37/0028* (2013.01);
(Continued)

(58) Field of Classification Search
CPC ............ A61M 5/31513; A61M 5/3129; B29C 37/0028; B29C 35/02; B29C 2037/0042;
(Continued)

(56) References Cited

U.S. PATENT DOCUMENTS

2003/0114802 A1 6/2003 Chung et al.
2006/0178643 A1 8/2006 Sudo et al.
(Continued)

FOREIGN PATENT DOCUMENTS

JP    7-025953 Y2    6/1995
JP    3282322 B2    5/2002
(Continued)

*Primary Examiner* — Ryan M Ochylski
(74) *Attorney, Agent, or Firm* — Birch, Stewart, Kolasch & Birch, LLP

(57) ABSTRACT

A laminated gasket (13) to be used for a medical syringe is provided, which includes a main body (14) made of an elastic material, and a film (15) provided on a surface of the main body (14). The gasket (13) has a circumferential surface portion (17) to be brought into contact with an inner peripheral surface (16) of a syringe barrel (11) of the syringe. The gasket (13) further includes a projection (22) provided on a surface portion of the film (15) present in the circumferential surface portion (17) as extending circumferentially of the gasket. The projection (22) has a height of not less than 15 μm and not greater than 55 μm and a width of not less than 30 μm and not greater than 75 μm. With this arrangement, the laminated gasket is excellent in sealability.

14 Claims, 2 Drawing Sheets

(51) Int. Cl.
*B29C 37/00* (2006.01)
*A61M 5/31* (2006.01)
*B29K 21/00* (2006.01)
*B29K 105/00* (2006.01)
*B29L 31/26* (2006.01)
*B29L 31/00* (2006.01)

(52) U.S. Cl.
CPC ............ *A61M 2005/3131* (2013.01); *A61M 2205/0216* (2013.01); *A61M 2207/00* (2013.01); *B29C 35/02* (2013.01); *B29C 2037/0042* (2013.01); *B29K 2021/00* (2013.01); *B29K 2105/256* (2013.01); *B29L 2031/265* (2013.01); *B29L 2031/7544* (2013.01)

(58) Field of Classification Search
CPC ......... B29K 2021/00; B29K 2105/256; B29L 2031/265; B29L 2031/7544; B33Y 10/00; B33Y 30/00; B33Y 50/00; B33Y 50/02
See application file for complete search history.

(56) References Cited

U.S. PATENT DOCUMENTS

| | | |
|---|---|---|
| 2013/0040156 A1 | 2/2013 | Nakano et al. |
| 2013/0053786 A1* | 2/2013 | Maeda ................ B29C 33/3842 |
| | | 425/112 |
| 2013/0316110 A1 | 11/2013 | Sudo |
| 2016/0287800 A1 | 10/2016 | Nakano et al. |
| 2017/0106594 A1* | 4/2017 | Gardiner ............... B29C 70/384 |
| 2017/0260359 A1* | 9/2017 | Hanyu ...................... B32B 1/00 |

FOREIGN PATENT DOCUMENTS

| | | |
|---|---|---|
| JP | 2003-190283 A | 7/2003 |
| JP | 2004-8509 A | 1/2004 |
| JP | 2004-162761 A | 6/2004 |
| JP | 2006-181027 A | 7/2006 |
| JP | 4908617 B2 | 4/2012 |
| JP | 2013-244668 A | 12/2013 |
| JP | 2015-146871 A | 8/2015 |
| WO | WO 2015/118958 A | 8/2015 |
| WO | WO-2016158052 A1 * | 10/2016 |

* cited by examiner

MEDICAL SYRINGE, GASKET TO BE USED FOR SYRINGE, AND GASKET PRODUCTION METHOD

CROSS-REFEENCE TO RELATED APPLICATIONS

This application is a Divisional of copending application Ser. No. 15/640,816, filed on Jul. 3, 2017, which claims priority under 35 U.S.C. § 119(a) to Application No. 2016-153119, filed in Japan on Aug. 3, 2016, all of which are hereby expressly incorporated by reference into the present application.

TECHNICAL FIELD

The present invention relates to a medical syringe, particularly to a gasket to be used for the medical syringe, and a gasket production method.

BACKGROUND ART

Syringes prefilled with a liquid drug (generally referred to as "prefilled syringes") are used as medical syringes. The prefilled syringes are advantageous because of their handling ease without the need for transferring the liquid drug into the syringes. Further, transfer of a wrong liquid drug into the syringe is advantageously prevented. Therefore, the prefilled syringes are increasingly used in recent years.

Unlike conventional syringes into which a liquid drug sucked up from a vial or other container is transferred immediately before use, the prefilled syringes are each required to serve as a container which is kept in contact with the liquid drug for a long period of time.

Such a syringe typically includes a syringe barrel, a plunger reciprocally movable in the syringe barrel, and a gasket attached to a distal end of the plunger.

The gasket to be used for the syringe is generally made of a crosslinked rubber. It is known that the crosslinked rubber contains various crosslinking components, and these crosslinking components and their thermally decomposed products are liable to migrate into the liquid drug when the liquid drug is kept in contact with the gasket. It is also known that these migrating components adversely influence the efficacy and the stability of some liquid drug.

Further, the gasket is required to be smoothly slidable when the syringe is used. In general, the gasket made of the crosslinked rubber is poorer in slidability. To cope with this, it is a general practice to apply silicone oil to an inner surface of the syringe barrel. However, it is also known that the silicone oil adversely influences the efficacy and the stability of some liquid drugs.

From this viewpoint, a product of so-called "laminated gasket" including a rubber gasket body having a surface laminated with a highly slidable film is often used for the medical syringe. Since the surface of the rubber gasket body of the laminated gasket is covered with the highly slidable film, it is possible to prevent the components of the crosslinked rubber from migrating into the liquid drug, and to ensure the slidability even without the use of the silicone oil.

CITATION LIST

Patent Document

Patent Document 1: JP-HEI7(1995)-25953-U

SUMMARY OF THE INVENTION

Problem to be Solved by the Invention

In the laminated gasket, however, the film to be used for the lamination of the surface is not elastic and, therefore, is liable to impair the elasticity of the inside crosslinked rubber. The elasticity of the overall gasket is an essential requirement for reliable sealing of the liquid drug contained in the syringe barrel. If the gasket has insufficient elasticity, the liquid drug contained in the syringe barrel is liable to leak out of the syringe barrel.

The inventors of the present invention conducted studies to cope with these problems and, as a result, conceived that the problems can be solved by forming a minute groove structure in a circumferential surface portion of the gasket after the gasket body laminated with the film is formed by molding, and further conducted studies.

If laser processing is performed at a higher energy for the formation of the minute groove structure, however, not only the outer film but also the underlying rubber gasket body is processed and, therefore, the rubber gasket body is liable to be exposed or damaged.

To cope with this problem, the inventors further conducted studies and, as a result, found that the problems can be solved by additionally forming a projection on the film of the laminated gasket rather than by forming the groove in the circumferential surface portion of the gasket.

In view of the foregoing, it is an object of the present invention to provide a laminated gasket ensuring excellent sealability for a medical syringe, and to provide a production method for the laminated gasket.

Solution to Problems

According to the present invention, there is provided a laminated gasket to be used for a medical syringe, the gasket including a main body made of an elastic material, and a film provided on a surface of the main body, the gasket having a circumferential surface portion to be brought into contact with an inner peripheral surface of a syringe barrel of the syringe, the gasket further including a projection provided on a surface portion of the film present in the circumferential surface portion as extending circumferentially of the gasket.

The projection desirably has a height of not less than 15 µm and not greater than 55 µm.

The projection desirably has a width of not less than 30 µm and not greater than 75 µm.

The projection desirably includes at least one annular projection extending circumferentially of the circumferential surface portion.

The film desirably has a thickness of not less than 20 µm and not greater than 50 µm.

A medical syringe according to the present invention includes a tubular syringe barrel, a plunger combined with the syringe barrel and reciprocally movable in the syringe barrel, and a gasket attached to a distal end of the plunger, wherein the gasket is the inventive gasket described above.

The medical syringe is a prefilled syringe in which the syringe barrel is prefilled with a liquid drug.

A method for producing the inventive laminated gasket includes the steps of: preparing a gasket molding mold; molding a gasket in the mold, the gasket having a surface laminated with a film and including a circumferential surface portion; removing the gasket from the mold, and then forming a projection of a fluid material on the circumferential surface portion of the gasket circumferentially of the circumferential surface portion; and solidifying the formed fluid material projection.

The gasket molding step includes the step of stacking an unvulcanized rubber on an inner surface of the film in the mold, and vulcanization-molding the rubber.

The gasket molding step includes the step of roughening the inner surface of the film before stacking the rubber on the inner surface of the film.

The fluid material includes a fluororesin.

The fluid material includes a metal paste.

The projection solidifying step includes a heating step.

Effects of the Invention

According to the present invention, the laminated gasket for the medical syringe is excellent in sealability. The laminated gasket is particularly suitable for a prefilled syringe.

According to the present invention, the medical syringe, particularly the prefilled syringe, is excellent in sealability, and free from adverse influence on the efficacy and the stability of a liquid drug even if the syringe is kept in contact with the liquid drug for a long period of time.

In the present invention, where the projection provided on the surface of the film has a height of 1 μm to 50 μm and a width of 1 μm to 70 μm, the liquid leakage can be more advantageously prevented.

According to the present invention, the gasket production method is employed for producing a laminated gasket having excellent sealability.

EMBODIMENTS OF THE INVENTION

With reference to the attached drawings, one embodiment of the present invention will hereinafter be described specifically.

Figure 1:
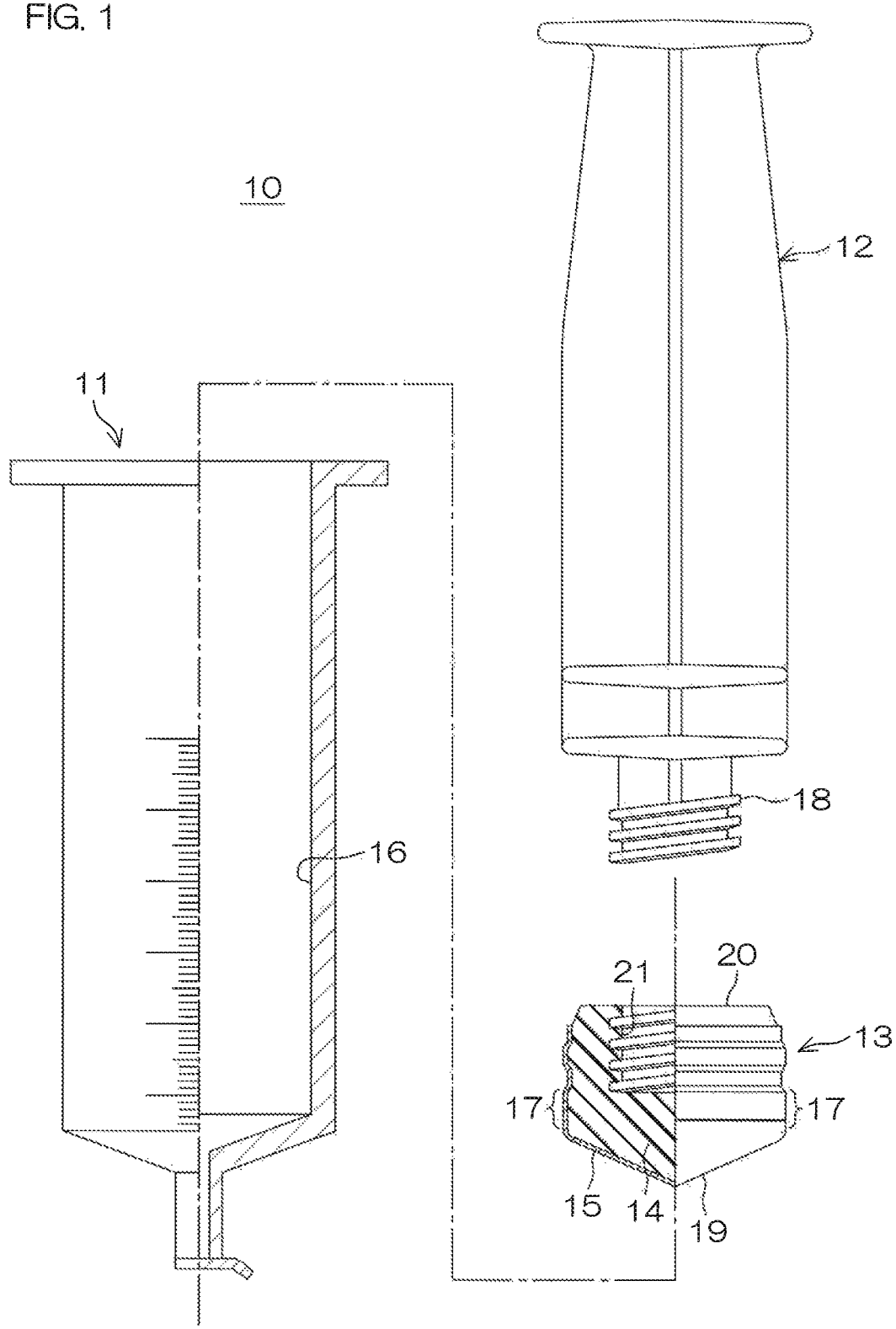
FIG. 1 is an exploded diagram illustrating a medical syringe according to an embodiment of the present invention.

FIG. 1 is an exploded diagram illustrating a medical syringe, i.e., a so-called prefilled syringe, according to the embodiment of the present invention. In FIG. 1, a half of a syringe barrel 11 and a half of a gasket 13 are illustrated in section.

Referring to FIG. 1, the prefilled syringe 10 includes a hollow cylindrical syringe barrel 11, a plunger 12 combined with the syringe barrel 11 and reciprocally movable in the syringe barrel 11, and a gasket 13 attached to a distal end of the plunger 12. The gasket 13 is a so-called laminated gasket, which includes a main body 14 made of an elastic material (a rubber or an elastomer) and a film 15 provided on a surface of the main body 14. The gasket 13 has a circumferential surface portion 17 to be kept in gas-tight and liquid-tight contact with an inner peripheral surface 16 of the syringe barrel 11.

The plunger 12 includes a resin plate piece, for example, having a cross shape as seen in section, and a head 18 provided at a distal end of the resin plate piece and fitted with the gasket 13. The head 18 is an integral part of the plunger 12 made of a resin and shaped in a male screw.

The gasket 13 has a generally cylindrical shape having a short axis. The gasket 13 has a distal end face 19, for example, having a conical center portion projecting at an obtuse angle, and a rear end face 20 axially recessed into an engagement recess 21 shaped in a female screw. The head 18 of the plunger 12 is screwed into the engagement recess 21 of the gasket 13, whereby the gasket 13 is attached to the distal end of the plunger 12.

Where a liquid drug to be contained in the syringe barrel 11 is not adversely influenced by generally used silicone oil or curable silicone, the silicone oil or the curable silicone may be applied on the inner surface 16 of the syringe barrel 11 or on a surface of the gasket 13 to ensure higher slidability of the gasket 13 with respect to the syringe barrel 11.

Figure 2:
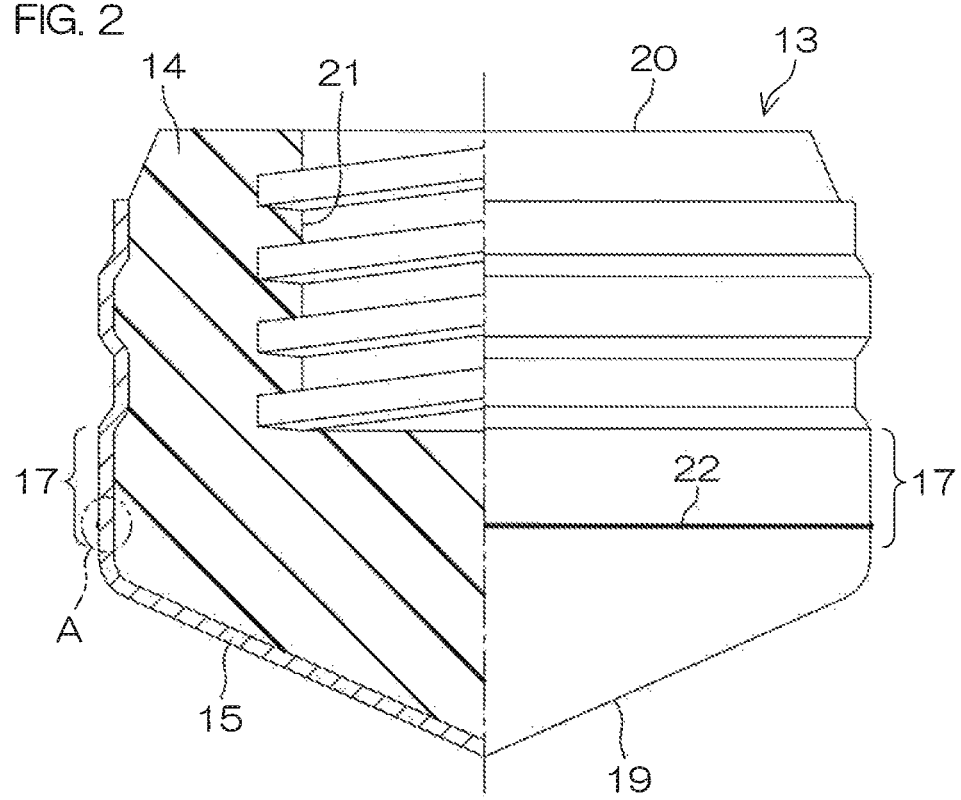
FIG. 2 is a diagram of a laminated gasket according to the embodiment of the present invention with a half of the gasket illustrated in section.

FIG. 2 is a diagram showing only the gasket 13 of FIG. 1 on an enlarged scale. In FIG. 2, a half of the gasket 13 is illustrated in section.

Referring to FIG. 2, the structure of the gasket 13 according to this embodiment will be described in greater detail.

The gasket 13 includes the main body 14, and the film 15 provided on the surface of the main body 14. The main body 14 is merely required to be made of the elastic material, which is not particularly limited. Examples of the elastic material include thermosetting rubbers and thermoplastic elastomers. Of these elastic materials, the thermosetting rubbers and dynamically crosslinkable thermoplastic elastomers having crosslinking sites are more preferred because of their excellent heat resistance. These polymer components for the elastic material are not particularly limited, but preferred examples include ethylene-propylene-diene rubbers and butadiene rubbers which are excellent in moldability. Other preferred examples include butyl rubbers, chlorinated butyl rubbers and brominated butyl rubbers which are excellent in gas barrier property.

The type of the film 15 to be provided on the surface of the main body 14 is not particularly limited, as long as the film is capable of preventing migration of substances from the crosslinked rubber (main body 14) and has more excellent slidability, i.e., a smaller friction coefficient, than the rubber. Examples of the film include films of ultrahigh molecular weight polyethylenes and fluororesins which are proved to be practical in medical applications. Particularly, the fluororesin films are preferred because they are excellent in slidability and have chemically stable surfaces. Usable examples of the fluororesins include conventionally known fluorine-containing resins such as PTFE, modified PTFE, ethylene tetrafluoroethylene copolymers (ETFE) and perfluoroalkyl ether (PFA). The PTFE and the modified PTFE are preferred because of their excellent slidability and chemical stability. The ETFE is also preferred because of its higher resistance to γ-ray to be used for sterilization. For adhesion to the main body 14, a film made of a mixture of these resins or a laminate film of these resins may be used.

An inner surface of the film to be provided on the main body 14 (to be kept in contact with the main body 14) is preferably processed for adhesion. The method for the adhesion processing is not particularly limited. A preferred example of the adhesion processing is an ion beam processing process which is unlikely to chemically alter the film and obviates the use of an adhesive agent.

Features of the laminated gasket 13 according to this embodiment are that the gasket 13 has the circumferential surface portion 17 to be kept in gas-tight and liquid-tight contact with the inner peripheral surface 16 of the syringe barrel 11, and that a projection 22 is provided on a surface portion of the film 15 present in the circumferential surface portion 17 as extending circumferentially of the gasket 13.

The projection 22 is an annular projection extending circumferentially of the circumferential surface portion 17. In this embodiment, a single projection 22 is provided by way of example.

It is merely necessary to provide at least one projection 22, but a plurality of projections may be provided so as to be axially spaced a predetermined distance from each other. There is no need to define an upper limit in the number of the projections. At least one of the projections should extend along the entire circumference of the circumferential surface portion 17. The other projections are not necessarily required to circumferentially annularly extend, but may be intermittent.

The projection 22 is preferably an annular projection extending circumferentially of the circumferential surface portion 17 from a start point to an end point located at the same position as the start point. With this arrangement, a liquid drug sealing effect is provided for uniformly sealing the liquid drug along the entire circumference of the circumferential surface portion 17. With the circumferential surface portion 17 of the gasket 13 being seen in a development elevation, the projection 22 preferably extends generally linearly without local directionality.

Figure 3:
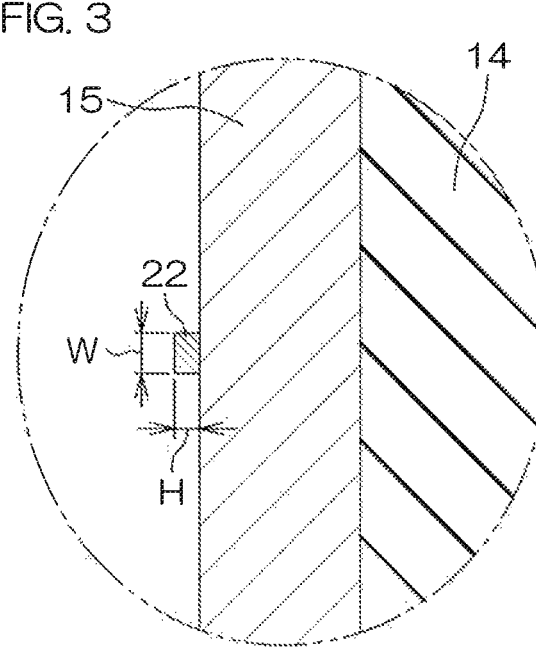
FIG. 3 is an enlarged sectional view of a portion A shown in FIG. 2.

FIG. 3 is an enlarged partial sectional view of the single projection 22 provided on the circumferential surface portion 17 of FIG. 2, i.e., an enlarged sectional view of a portion A shown in FIG. 2.

The effect of the present invention can be ensured by first molding a gasket and then forming a projection 22 on the gasket. If the molding of the gasket and the formation of the projection are achieved simultaneously, i.e., if a mold preliminarily formed with a structure corresponding to the projection for transferring the projection structure is used for the molding, the projection structure formed by the molding is liable to be scratched or damaged during demolding of the resulting gasket, but this is prevented by the aforementioned arrangement. Further, scratches and the like occurring during the molding and the demolding of the gasket can be repaired to some extent by forming the projection 22 in the projection forming step subsequent to the molding step.

The projection forming step desirably includes the steps of forming a projection of a fluid material on a base of the laminated gasket 13, and solidifying the fluid material projection thus formed.

The use of the fluid material is advantageous in that the formation of the fluid material projection is achieved by a simple method, for example, by applying the fluid material. A known method such as a printing method, a spray coating method or the like may be used for the formation of the fluid material projection (for the application of the fluid material).

The fluid material is not particularly limited, as long as it is capable of withstanding the subsequent solidifying step. A fluororesin is preferred for the fluid material, because it has a smaller friction coefficient after being solidified and, as a result, reduces the sliding resistance of the gasket in the syringe barrel. Examples of the fluid material include an emulsion containing the fluororesin and a paste containing the fluororesin dispersed in an organic solvent. Examples of the fluororesin include PTFE, modified PTFE, ethylene tetrafluoroethylene copolymers (ETFE) and perfluoroalkyl ether (PFA). The PTFE and the modified PTFE are particularly preferred because of their excellent slidability and chemical stability. The ETFE is preferred because of its higher resistance to γ-ray to be used for sterilization. Metal pastes are also preferred because of their excellent thermal stability and relatively low solidification temperatures.

The step of solidifying the fluid material projection is not particularly limited, but a heating method is preferably employed for the solidification. The fluid material projection is solidified to be bonded to the film 15 by the heating, and the resulting projection 22 is prevented from being separated from the film 15 when the gasket 13 is slid in the syringe barrel 11. For the heating, the base of the laminated gasket 13 formed with the fluid material projection is put in a heating furnace.

The heating temperature is preferably not higher than 200° C., more preferably not higher than 150° C., for suppression of damage to the base. Another heating method which suppresses the damage to the base is to heat only the fluid material projection. A laser beam may be applied only to the fluid material projection for heating the fluid material projection by way of example but not by way of limitation. The laser beam is not particularly specified, but is preferably a greater wavelength laser beam having a higher heating effect and a lower decomposing effect. In this case, the projection 22 is formed as having a desired shape by applying the fluid material to a width greater than the width of the desired projection shape, partly heating the applied fluid material to solidify a desired portion of the applied fluid material, and washing off the rest of the fluid material.

Another method for the formation of the projection 22 is to fluidize a thermoplastic resin by heating, applying the fluidized thermoplastic resin, and solidifying the thermoplastic resin by cooling.

The formed projection 22 preferably has a height H of not less than 1 μm and not greater than 50 μm, more preferably not less than 15 μm and not greater than 35 μm. Further, the projection 22 has a width W of not less than μm and not greater than 70 μm, more preferably not less than 10 μm and not greater than 40 μm. A feature of the present invention is that only the projection 22 is kept in contact with the inner peripheral surface 16 of the syringe barrel 11 around the projection 22 to increase a contact pressure between the gasket 13 and the syringe barrel 11. The projection 22 preferably has a smaller size for increasing the contact pressure. For processing ease, on the other hand, it is not preferred to excessively reduce the size of the projection 22.

Next, a method for producing the gasket 13 according to this embodiment will be described. The gasket 13 according to this embodiment is produced through the following production process steps:

(1) preparing a gasket molding mold;
(2) molding a gasket laminated with a film in the mold;
(3) removing the laminated gasket from the mold, and then forming a projection of a fluid material on a circumferential surface portion of the gasket circumferentially of the circumferential surface portion; and
(4) solidifying the fluid material projection.

In the step of molding the gasket laminated with the film in the mold, an unvulcanized rubber is put on an inner surface of the film in the mold, and vulcanization-molded.

For example, a sheet of an unvulcanized rubber containing a crosslinking agent is stacked on the film, and vulcanization-molded in the mold. Thus, the gasket is produced as having a predetermined shape.

In this case, the inner surface of the film 15 on which the rubber is to be put is preferably preliminarily roughened. With the inner surface of the film 15 roughened, the rubber can firmly adhere to the film 15 by the vulcanization molding without the use of an adhesive agent or the like. The adhesion is attributable to an anchoring effect which is created with the vulcanized rubber intruding into voids formed in the roughened inner surface of the film 15.

The modification (roughening) of the inner surface of the film 15 may be achieved, for example, by applying ion beam to the inner surface to break the internal molecular structure in the inner surface (see, for example, JP4908617B).

The gasket 13 is produced as having excellent sealability by molding the gasket in the mold and then forming the projection 22. The method for forming the projection 22 after the molding of the gasket (including the steps of forming the fluid material projection, and solidifying the fluid material projection) is previously described.

EXAMPLES

Examples 1 to 5 and Comparative Example 1

Gasket structures were produced by using fluororesin films and an unvulcanized rubber sheet. More specifically, the films were each preliminarily subjected to an adhesion process. The unvulcanized rubber sheet was stacked on the film, and the gasket structures were each produced by vulcanization-molding the resulting stack. Then, gaskets (Examples 1 to 5) were each produced by forming a projection of a fluid material on the gasket structure and solidifying the fluid material projection, and a gasket (Comparative Example 1) was produced without forming a projection.

In Examples 1 to 5 and Comparative Example 1, the resulting gaskets were kept at 121° C. for one hour in a high-pressure steam sterilization apparatus for cleaning.
[Production Method]

Colorless and colored PTFE films (CHEMFILM (registered trade name) DF1200 available from Saint-Gobain Corporation) were used as the fluororesin films.

The adhesion process for the films was performed by the method described in JP4908617B. Both surfaces of each of the films were subjected to the adhesion process. The thicknesses of the films herein used are shown in Table 1. The thicknesses of the films after the molding were generally about one third the original thicknesses.

A halogenated butyl rubber was used as a material for the unvulcanized rubber sheet.

2-di-n-butylamino-4,6-dimercapto-s-triazine (Zisnet DB (registered trade name) available from Sankyo Kasei Co., Ltd.) was used as a crosslinking agent.

A vulcanization temperature of 180° C., a vulcanization period of 8 minutes and a processing pressure of 20 MPa were employed for production conditions.

The gaskets each had a product shape having a maximum diameter of 6.60 mm.

The formation and the solidification of the fluid material projection were performed after the production of the gasket structure.
[Fluid Material for Projection, and Formation of Fluid Material Projection]

A fluororesin dispersion (POLYFLON D210-C available from Daikin Industries, Ltd.) and an electrically conductive paste of a thermosetting type containing silver particles (CA-6178 available from Daiken Chemical Co., Ltd.) were used as the fluid material.

With the use of a micro-dispenser (available from Heishin, Ltd.), the fluid material was applied onto each of the gasket structures while the gasket structure was rotated circumferentially. With the dispensing rate of the fluid material kept constant, the gasket structures were rotated at different rotation speeds so that the projections of the fluid material were formed on the respective gasket structures as having different dimensions in Examples 1 to 5.
[Heating Process]

After the formation of the fluid material projection on each of the gasket structures, a preliminary drying process was performed at 80° C. for one hour, and then a heating process was performed by either of the following methods:
A. Heating in Oven The heating process was performed by maintaining the gasket structure in an oven set at a predetermined temperature (200° C. or 130° C.) for one hour.
B. Heating by Laser Beam A multi-purpose manually-operable machine available from Allied Lasers, Inc. was used for the heating process. A laser beam having a wavelength of 1064 nm was emitted with the use of a hybrid laser as an oscillator. The laser beam for the heating process had a spot diameter of 10 μm.
[Test Method]
Measurement of Dimensions of Projection By means of a laser microscope (VK-X100 available from Keyence Corporation), the surface geometry of each of the gasket products formed with the solidified projections was measured with an objective lens having a magnification of 50×. For each of the gasket products, the maximum height and the width of the projection were measured at four positions on an image of the gasket product, and arithmetic averages were determined for the maximum height and the width.
Liquid Drug Sealability The gasket products thus produced were each inserted in a syringe barrel, which was in turn filled with a test liquid. Then, an opposite end of the syringe barrel was capped. The resulting syringe barrel was allowed to stand still at 40° C. for one week, and then observed with an objective lens having a magnification of 50× by means of a video microscope (DVM5000 available from Leica Microsystems Inc.) to be checked for liquid leakage. For each of the gasket products, 20 samples were prepared, and the number of samples suffering from liquid leakage (in which the test liquid penetrated beyond a maximum diameter portion) is shown in Table 1. A gasket product with three or less samples suffering from the liquid leakage was rated as acceptable. The test liquid herein used was prepared by adding 0.2 g/L of a colorant (Methylene Blue available from Sigma Aldrich Japan LLC.) and 1.0 g/L of a surfactant (POLYSORBATE 80 available from NOF Corporation) to water. The syringe barrel herein used was a syringe barrel of a cycloolefin resin having an inner diameter of 6.35 mm.

TABLE 1

|  | Example 1 | Example 2 | Example 3 | Example 4 | Example 5 | Comparative Example 1 |
| --- | --- | --- | --- | --- | --- | --- |
| Type of film | PTFE | PTFE | PTFE | PTFE | PTFE | PTFE |
| Thickness (μm) of film | 25 | 25 | 25 | 25 | 25 | 25 |
| Fluid material | PTFE | PTFE | Metal paste | Metal paste | PTFE | — |

TABLE 1-continued

|  | Example 1 | Example 2 | Example 3 | Example 4 | Example 5 | Comparative Example 1 |
|---|---|---|---|---|---|---|
| Maximum height of projection | 55 | 30 | 50 | 15 | 25 | — |
| Width of projection | 75 | 35 | 60 | 30 | 35 | — |
| Heating method | A | A | A | A | B | — |
| Heating temperature | 200 | 130 | 130 | 130 | — | — |
| Liquid drug sealability | 3 | 1 | 2 | 1 | 0 | 6 |

[Test Results]

The gaskets of Examples 1 to 5 each had a significantly smaller number of samples suffering from the liquid leakage than the gaskets of Comparative Example 1 formed with no projection after the molding of the gasket structure.

This application corresponds to Japanese Patent Application No. 2016-153119 filed in the Japan Patent Office on Aug. 3, 2016, the disclosure of which is incorporated herein by reference in its entirety.

The invention claimed is:

1. A method for producing a gasket to be used for a medical syringe, the method comprising the steps of:
    preparing a gasket molding mold which has a cavity for forming an exterior surface of a gasket;
    covering at least a portion of an unvulcanized rubber substrate with a film wherein an inner surface of the film is adhered to the unvulcanized rubber substrate to form a covered unvulcanized rubber substrate;
    disposing the covered unvulcanized rubber substrate in the mold cavity with the film outer surface facing the mold cavity;
    vulcanization-molding the covered unvulcanized rubber substrate in the mold to form a gasket that has a surface at least partially laminated with the film and includes a circumferential surface portion laminated with the film that extends circumferentially about the gasket;
    removing the gasket from the mold, and then forming a line-shaped projection of a fluid material circumferentially about the gasket on the circumferential surface portion of the gasket; and
    solidifying the formed fluid material projection.

2. The gasket producing method according to claim 1, wherein the step of covering the unvulcanized rubber substrate with the film includes a step of roughening the inner surface of the film before stacking the unvulcanized rubber substrate is covered with the film.

3. The gasket producing method according to claim 1, wherein the fluid material comprises a fluororesin.

4. The gasket producing method according to claim 1, wherein the fluid material comprises a metal paste.

5. The gasket producing method according to claim 1, wherein the step of solidifying the formed fluid material projection includes a heating step.

6. The gasket producing method according to claim 3, wherein the step of solidifying the formed fluid material projection includes a heating step.

7. The gasket producing method according to claim 4, wherein the step of solidifying the formed fluid material projection includes a heating step.

8. The gasket producing method according to claim 1, wherein the line-shaped projection is an annular projection extending circumferentially about the circumferential surface portion from a start point to an end point located at the same position as the start point.

9. The gasket producing method according to claim 8, wherein the line-shaped projection extends generally linearly about the circumferential surface portion of the gasket when viewed in a development elevation.

10. The gasket producing method according to claim 1, wherein a width of the line-shaped projection is narrower than a width of the circumferential surface portion.

11. The gasket producing method according to claim 1, wherein a width of the line-shaped projection is not less than 1 μm and not greater than 70 μm.

12. The gasket producing method according to claim 11, wherein the width of the line-shaped projection is not less than 10 μm and not greater than 40 μm.

13. The gasket producing method according to claim 1, wherein a height of the line-shaped projection is not less than 1 μm and not greater than 50 μm.

14. The gasket producing method according to claim 13, wherein the height of the line-shaped projection is not less than 15 μm and not greater than 35 μm.

* * * * *